(12) United States Patent
Doepker et al.

(10) Patent No.: US 7,207,168 B2
(45) Date of Patent: Apr. 24, 2007

(54) APPARATUS AND METHOD FOR INSERTING STAPLE DRIVERS IN A CARTRIDGE

(75) Inventors: Brian T. Doepker, Kalida, OH (US); David B. Erhart, Kalida, OH (US); Ronald J. Schnipke, Cloverdale, OH (US)

(73) Assignee: The Schnipke Family Limited Liability Company, Ottoville, OH (US)

( * ) Notice: Subject to any disclaimer, the term of this patent is extended or adjusted under 35 U.S.C. 154(b) by 141 days.

(21) Appl. No.: 10/994,081

(22) Filed: Nov. 19, 2004

(65) Prior Publication Data

US 2006/0107645 A1 May 25, 2006

(51) Int. Cl.
*B29C 37/02* (2006.01)
*B29C 65/00* (2006.01)
*B23Q 3/00* (2006.01)

(52) U.S. Cl. ............... 59/71; 59/77; 29/464; 29/811.2; 264/138; 264/249; 227/110; 227/120; 227/176.1

(58) Field of Classification Search .................. 59/71, 59/77; 29/464, 811.2; 264/138, 249; 227/110, 227/120, 176.1; 606/143, 144
See application file for complete search history.

(56) References Cited

U.S. PATENT DOCUMENTS

| | | | | |
|---|---|---|---|---|
| 3,751,902 A | * | 8/1973 | Kingsbury et al. ............. 59/71 |
| 3,894,174 A | * | 7/1975 | Cartun ............................ 59/77 |
| 4,193,181 A | * | 3/1980 | Boulanger et al. ............ 29/509 |
| 4,612,933 A | * | 9/1986 | Brinkerhoff et al. ...... 227/175.2 |
| 4,714,187 A | * | 12/1987 | Green .......................... 227/19 |
| 5,018,657 A | * | 5/1991 | Pedlick et al. ............ 227/178.1 |
| 5,392,509 A | * | 2/1995 | Cheswick .................. 29/283.5 |
| 5,653,928 A | | 8/1997 | Schnipke |
| 5,836,147 A | | 11/1998 | Schnipke |
| 6,158,205 A | | 12/2000 | Schnipke |
| 6,729,119 B2 | | 5/2004 | Schnipke |

* cited by examiner

*Primary Examiner*—David B. Jones
(74) *Attorney, Agent, or Firm*—Jason H. Foster; Kremblas, Foster, Phillips & Pollick (57) ABSTRACT

An improved method and apparatus for inserting surgical staple drivers into a cartridge, including a base, a cartridge-receiving plate having a channel, upper and lower degating plates having a passage through them, a knife with a sharp edge adjacent the passage and a plunger apparatus that drives the drivers downwardly through the guide passage and into pockets in the cartridge. A cartridge locator plate seats the cartridge against stops in the channel. The cartridge-receiving plate is adjustable relative to the base. The upper and lower degating plates and the knife are not adjustable relative to the base, which avoids the need for re-alignment of the knife and degating plates upon re-mounting on the base. The cartridge-receiving plate is aligned relative to the base. A top riser is adjustably mounted to the base, and a cylinder arm, which holds the plunging apparatus, is non-adjustably mounted to the top riser.

22 Claims, 11 Drawing Sheets

APPARATUS AND METHOD FOR INSERTING STAPLE DRIVERS IN A CARTRIDGE

(e) BACKGROUND OF THE INVENTION

1. Field of the Invention

The present invention relates generally to an apparatus and method for inserting discrete articles into cartridges. More particularly, the present invention relates to an improved device and method for inserting staple drivers into surgical stapling cartridges.

2. Description of the Related Art

In the field of microsurgery, a surgical instrument having a cutting blade traverses a specific path through tissue. One feature of the surgical instrument is a single-use cartridge that is a holder for surgical staples. The cartridge is an elongated rectangular plastic body with a longitudinal channel, that serves as a guide for the surgical blade, having rows of small staples on opposite sides of the channel. The staples in the cartridge are aligned parallel to the guide channel. After the blade makes its cut, and other necessary surgical operations are performed, each side of the incision is stapled together to close the incision. In order to push the staples into the tissue adjacent the cartridge, drivers are inserted in the cartridge to push the staples out of the cartridge and through the tissue against an anvil on the opposing side of the surgical instrument as the cartridge, thereby deflecting the points of the staples into a clasping position.

There may be as many as fifty or more very small staples on each side of a two inch incision. Each staple can be driven simultaneously into the tissue to close the incision by the correspondingly small drivers. Insertion of the drivers into the cartridge and maintaining them in place to drive the staples into the tissue is a labor-intensive chore due to the small size of the drivers.

One prior art system for mounting the staple drivers into apertures, which are also called "pockets", in the cartridge includes a plastic holder, commonly referred to as a "tree" having aligned "branches" with drivers integrally formed on an end of each of the aligned branches. The conventional cartridge is placed in an apparatus and the tree with the drivers is hand-manipulated to place the drivers adjacent the entrance to the pockets. This is normally accomplished by inserting the drivers in funnel-shaped passages that are aligned with the pockets. Each driver is subsequently driven into the associated pocket of the cartridge. The separation of the individual drivers from the branch of the tree on which it is mounted is accomplished by flexing the branches of the tree manually to break the tree away from the staple drivers. Then, a hand-manipulated tool is used to press each staple driver down into the cartridge to near the pocket opening on the opposite side of the cartridge.

Unfortunately, the finger operation of pressing each driver into a pocket, the flexing of the branches and the subsequent pressing from the hand-operated prongs can misalign some of the drivers within the pockets. Furthermore, the sizes of the pockets and the drivers vary slightly due to the minute structure involved and the fact that both the cartridge and the staple drivers are formed of thermoplastic resin, which does not always result in a perfectly formed structure. This combination of factors can cause some "play" in the assembly, which can result in an alignment problem. In particular, inversion of the cartridge after assembly can result in some of the drivers being displaced from their pockets. If a staple driver is absent, no staple will be driven into the tissue at that point in the incision.

Another problem with the assembly is that of misalignment of the drivers with the cartridge. The drivers are inserted into the funnel-shaped passages on the fixture so as to align each individual driver with an associated pocket on the cartridge. However, the funnel-shaped passages do not fully cure the misalignment problem. Because the funnels do not fully engage the driver to be inserted, there is commonly some misalignment.

The misalignment of the driver within the pocket can cause additional problems. If the driver is not properly aligned, the staple which is ejected by use of the staple driver may be inaccurately bent during the surgery. In addition, the misalignment of the staple driver in the pocket can increase the force needed to eject a staple or prevent the ejection of that staple entirely.

Yet another problem is the imprecision in the process of separating the staple drivers from the branches of the plastic "tree", a process referred to as "degating." The drivers are mounted to the tree prior to insertion in the cartridge, but must be removed from the tree before or during the insertion process. Because the separation of a driver from the tree is not precise, it leaves some material on one side of each driver. The remnants of material left on the drivers is not a predictable size, and often the remnants are larger than desired. While it is not practical to remove all of the holder material from the side of each driver in the separation process, it is important that the amount of material left on each driver be relatively consistent between drivers. This is because the material left on the side tends to cause friction when the staple driver is used in surgery. If the amount of material left is consistent, it allows a user of such a staple cartridge to accurately predict the amount of force needed to expel a staple in surgery. In addition, the smaller the volume of material left, the less friction will be generated, and the less the force required to use the staple cartridge.

It is known in the prior art to insert drivers mechanically into surgical stapling cartridges, as shown in U.S. Pat. No. 5,836,147 to Schnipke, U.S. Pat. No. 5,635,928 to Schnipke, and U.S. Pat. No. 6,158,205 to Schnipke et al., all of which are incorporated herein by reference. These machines require people to position the cartridges and the holders that contain the drivers, and actuate the machine to insert the tiny drivers into the pockets in the cartridges. After a fraction of the total number of drivers is inserted by one machine, the cartridge is then manually transported to the next machine, which inserts another fraction of the drivers.

If any drivers are improperly inserted into a cartridge, or are not inserted, the cartridge is either discarded or repaired. Thus, errors in insertion of the tiny parts can result in wasted time and/or product.

Even the machines disclosed and claimed in the patents referenced above, although representing a significant improvement over the prior art, have problems, especially regarding ongoing maintenance. For example, it is difficult and costly to sharpen the knives that sever the drivers from the plastic trees. These knives are unitary parts of the degating plates that align the drivers over the apertures in the cartridge into which the drivers are driven, which means that any removal for sharpening means the degating apparatus must be removed. After removal and sharpening of the knives, the degating plates must be realigned with the entire machine, and this can be time-consuming and inexact.

In U.S. Pat. No. 6,729,119 to Schnipke et al., which is incorporated herein by reference, a robotic loader is discussed for use in filling the cartridges discussed herein.

However, this patent does not address the maintenance issues that continue to exist on the non-robotic devices discussed above.

Therefore, there is a need for an improved machine and method for loading drivers into surgical cartridges.

(f) BRIEF SUMMARY OF THE INVENTION

The invention is an apparatus for inserting a staple driver into a corresponding pocket formed in a surgical staple cartridge. The apparatus comprises a base and a cartridge-receiving plate rigidly and adjustably mounted to the base. The cartridge-receiving plate has a channel that is configured to receive the cartridge. A driver guide fixture is rigidly mounted to the base adjacent the channel of the cartridge-receiving plate. The guide fixture has a passage formed therein to receive and guide the driver into the cartridge during use. The guide fixture passage has a first portion with converging, tapered walls that guide the driver into alignment with the second portion that has walls with dimensions for fitting closely around at least part of the driver. A cutter is rigidly mounted to the base adjacent the channel and has at least one sharp edge for severing the driver from a driver holder. The sharp edge is disposed at an edge of the passage of the driver guide fixture, and the cutter is removable from the base separate from the driver guide fixture. A plunger apparatus has an element aligned with the fixture passage and configured to force the driver toward the fixture passage. This motion of the element thereby causes the driver holder to engage the sharp edge of the cutter and separate the driver from the driver holder, and the driver continues on into the pocket of the cartridge.

In the preferred embodiment, the cutter is non-adjustably mounted to the base, which means that it mounts in the same position from which it was removed. Furthermore, other structures, such as the cartridge-receiving plate, are adjusted relative to the cutter. Preferably, the guide fixture is also non-adjustably mounted to the base.

In a more preferred embodiment, stops are mounted near the channel of the cartridge-receiving plate, and a cartridge locator plate extends into the channel. The cartridge locator plate is actuated to seat against the cartridge and force the cartridge against the stops.

In a most preferred embodiment, a top riser is rigidly and adjustably mounted to the base, and an arm is rigidly and non-adjustably mounted to the top riser. The plunger apparatus is rigidly and non-adjustably mounted to said arm.

The invention also contemplates a method of inserting a driver into a pocket formed in a surgical staple cartridge. The method comprises mounting a cartridge-receiving plate to a base, where the cartridge-receiving plate has a channel configured to receive a cartridge. A driver guide fixture is rigidly mounted to the base adjacent the channel. The guide fixture has a passage formed therein to guide the driver into the cartridge. A cutter with a sharp edge is rigidly mounted to the base adjacent the channel. The method includes the steps of adjusting the position of the cartridge-receiving plate relative to the base to align the channel with the guide fixture passage, and adjusting the position of an element of a plunger apparatus relative to the base to align the element with the guide fixture passage. Then, the cartridge is positioned in the channel and the driver is positioned in the guide fixture passage, and the plunger is driven into engagement with the driver. This forces the driver through the guide fixture passage, forces the driver holder against the sharp edge of the cutter, separates the driver from the driver holder and forces the driver into the pocket of the cartridge. The final step of the method is the withdrawal of the plunger from the guide fixture passage.

In a preferred method, the cutter is removed from the base separate from the guide fixture, such as for sharpening, and then it can be re-mounted to the base without adjustment relative to the guide fixture. Additionally, the guide fixture can be removed from the base separate from the cutter.

In describing the preferred embodiment of the invention which is illustrated in the drawings, specific terminology will be resorted to for the sake of clarity. However, it is not intended that the invention be limited to the specific term so selected and it is to be understood that each specific term includes all technical equivalents which operate in a similar manner to accomplish a similar purpose. For example, the word connected or term similar thereto are often used. They are not limited to direct connection, but include connection through other elements where such connection is recognized as being equivalent by those skilled in the art.

(h) DETAILED DESCRIPTION OF THE INVENTION

Figure 1:
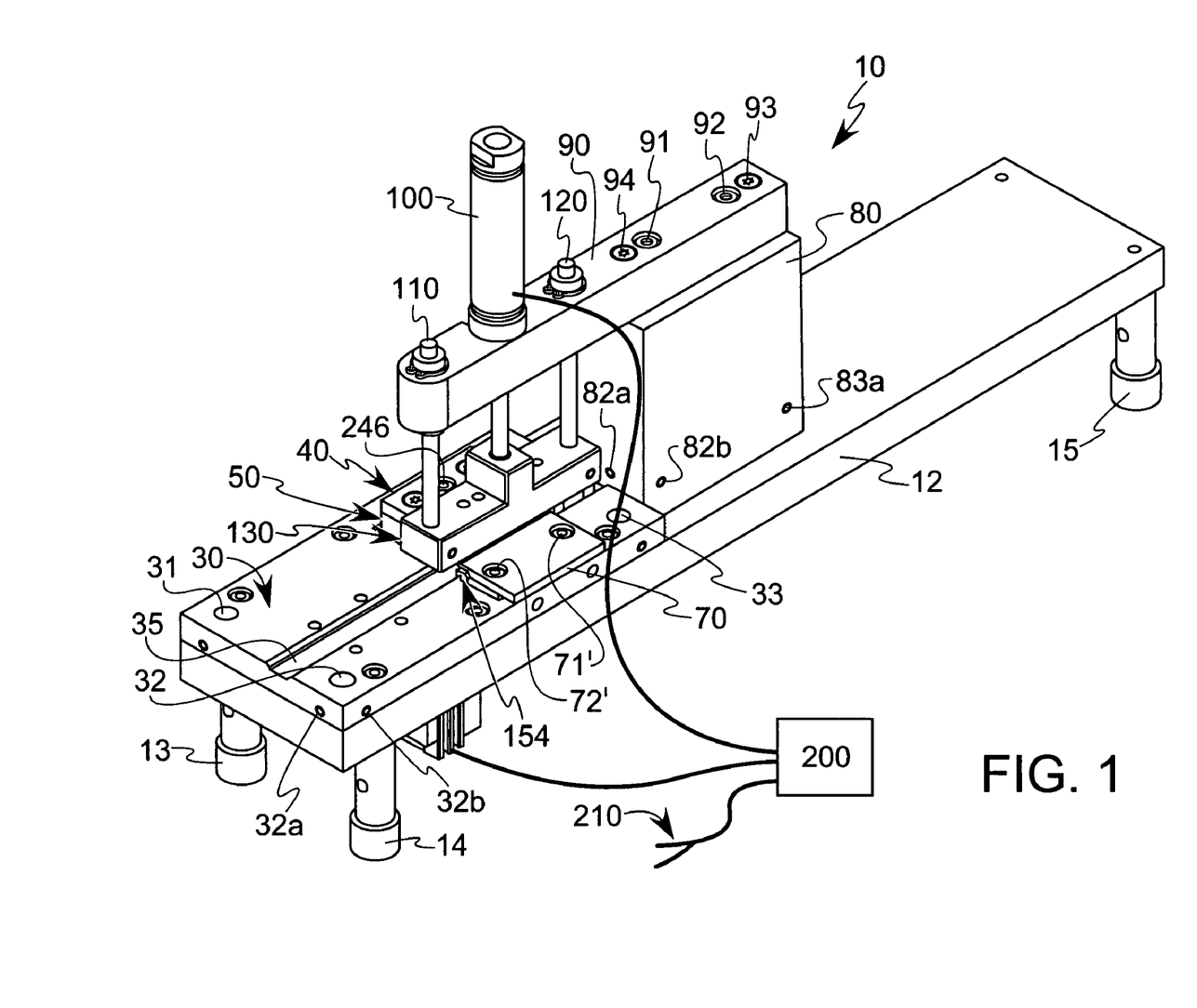
FIG. 1 is a view in perspective illustrating the preferred embodiment of the present invention.

The preferred staple driver insertion machine 10 is shown in FIG. 1 having a base 12 with four supporting legs 13, 14, 15 and 16 extending downwardly therefrom (leg 16 is not visible in FIG. 1, but is identical to the other legs and is located at the base's fourth corner). The supporting legs 13–16 are not essential, and can be replaced by other suitable support structures. When the machine 10 is in use, the legs are preferably seated at their lower ends against the upwardly facing surface of a table or workbench so that a worker can sit in front of the machine 10 while operating the same as described herein.

Figure 2:
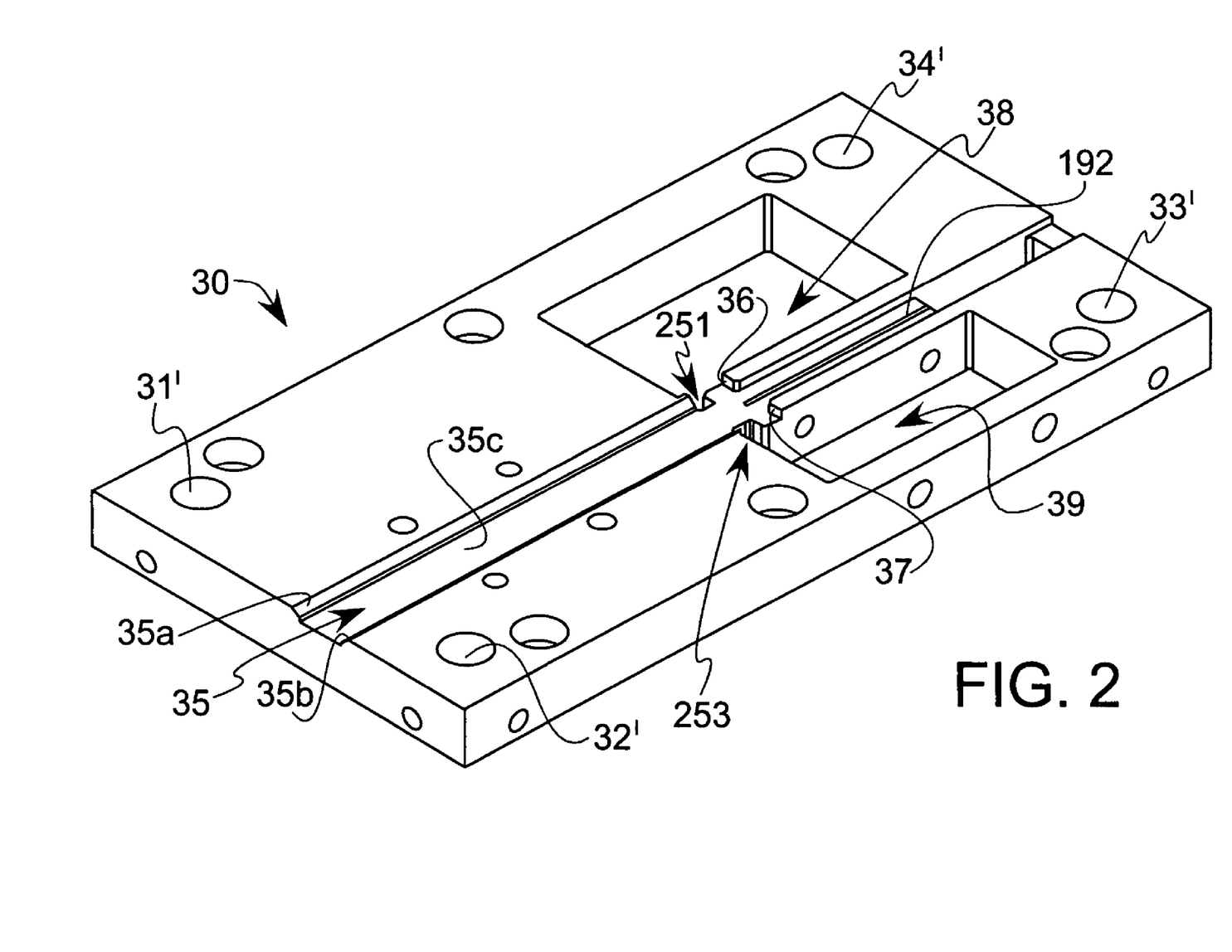
FIG. 2 is a view in perspective illustrating the preferred cartridge-receiving plate.

A cartridge-receiving plate 30 is mounted to the base 12 with means that permit adjustment of the position of the plate 30 relative to the base 12. In the embodiment shown in FIG. 1, there are four dowel pins 31, 32, 33 and 34 (pin 34 is not visible in FIG. 1) that extend loosely through the apertures 31', 32', 33' and 34' (see FIG. 2) in the corners of the plate 30 and extend rigidly into the base 12. Corresponding set screws, such as set screws 32a and 32b, extend parallel to the plane of the plate 30 through adjacent edges at each corner of the plate 30 and seat against the respective dowel pins 31–34. By tightening each pair of set screws against each dowel pin, the plate 30 becomes rigidly mounted to the dowel pins, and thereby, the base 12. Importantly, the plate 30 is also adjustably mounted relative to the base 12, because by adjusting each pair of set screws, one can adjust the position of the plate 30 relative to the dowel pins, and thereby, the base 12. Thus, by the combination of the dowel pins and corresponding set screws permit the plate 30 to be aligned relative to the base 12, and other parts that are mounted to the base 12.

Figure 13:
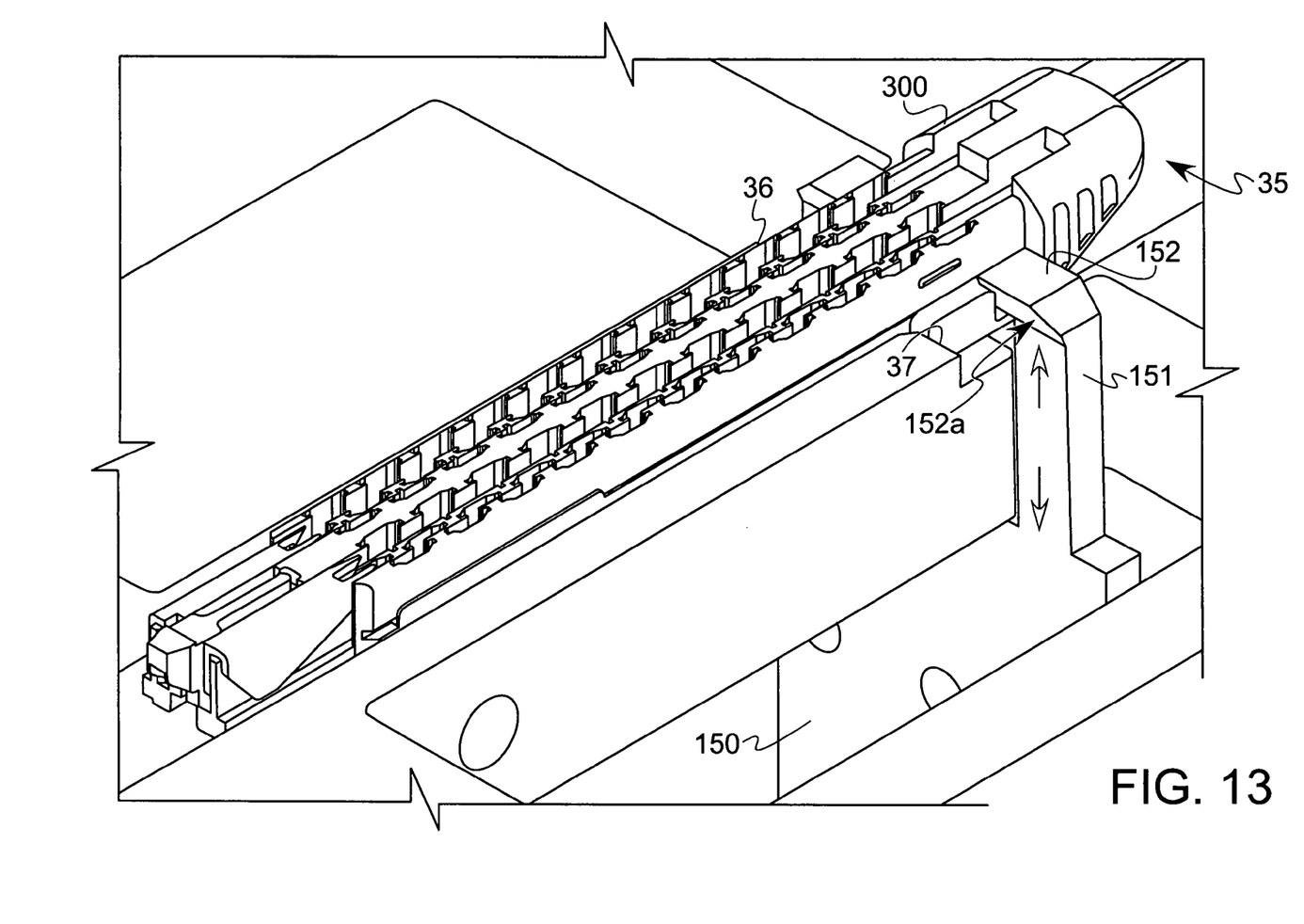
FIG. 13 is a view in perspective illustrating a portion of the present invention with a cartridge in an operable position.

The cartridge-receiving plate 30 has a channel 35 formed longitudinally in a major surface thereof, preferably the surface that faces upwardly during use. The channel 35 is defined by two sidewalls 35a and 35b and a floor 35c, against which a cartridge 300 seats for guidance during insertion, and for stability once inserted, into the machine 10 as shown in FIG. 13. Two stops 36 and 37 are formed near one end of the channel 35 for surfaces of the cartridge to seat against as described below.

The openings 38 and 39 extend completely through the plate 30 from a lower surface to the upper surface. When the plate 30 is mounted to the base 12, the openings permit structures to extend through the plate 30 and mount directly to the base 12 without contacting the plate 30.

Figure 3:
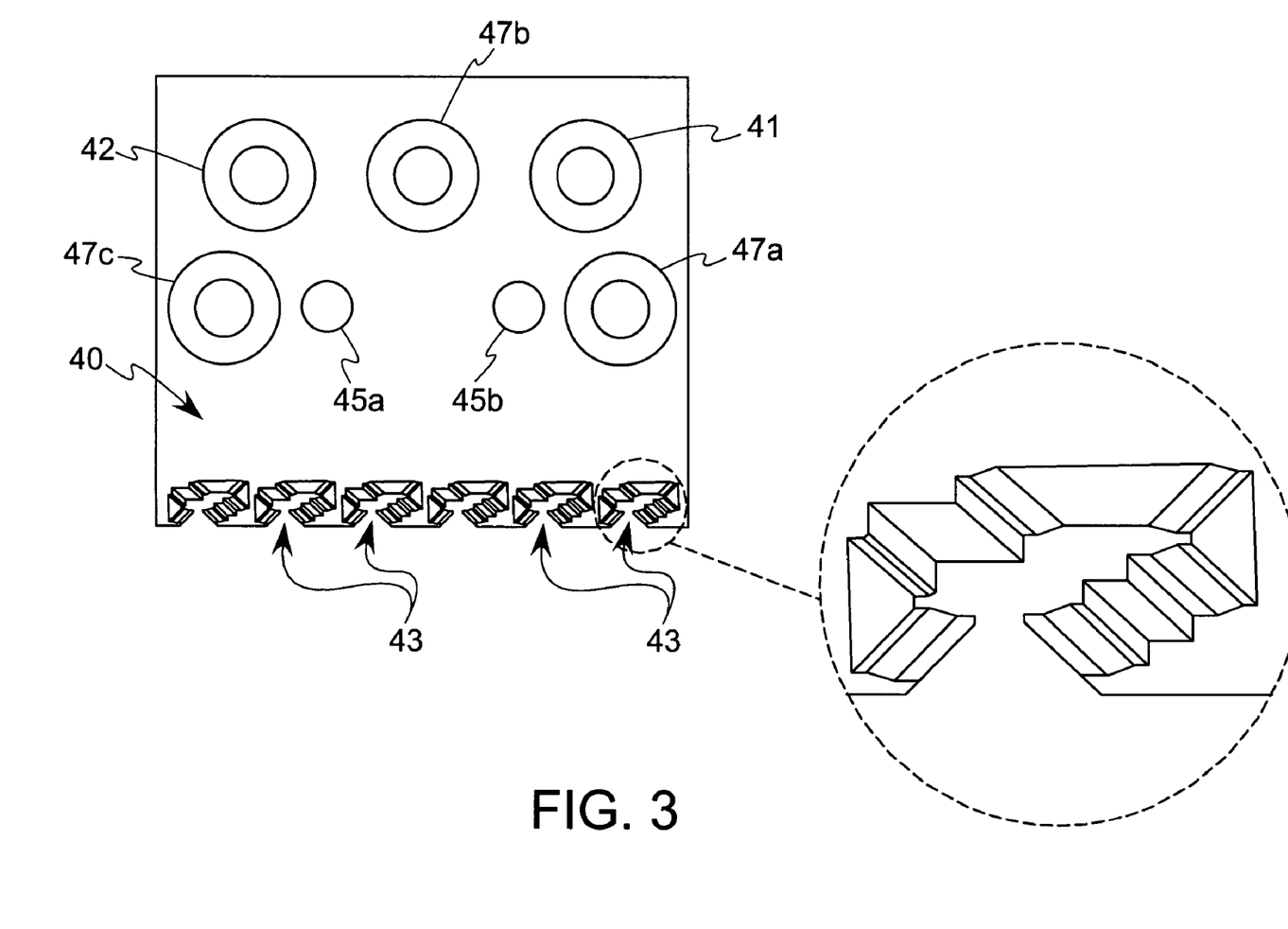
FIG. 3 is a top view illustrating the preferred upper degating plate with a section of an aperture through the plate magnified.
Figure 4:
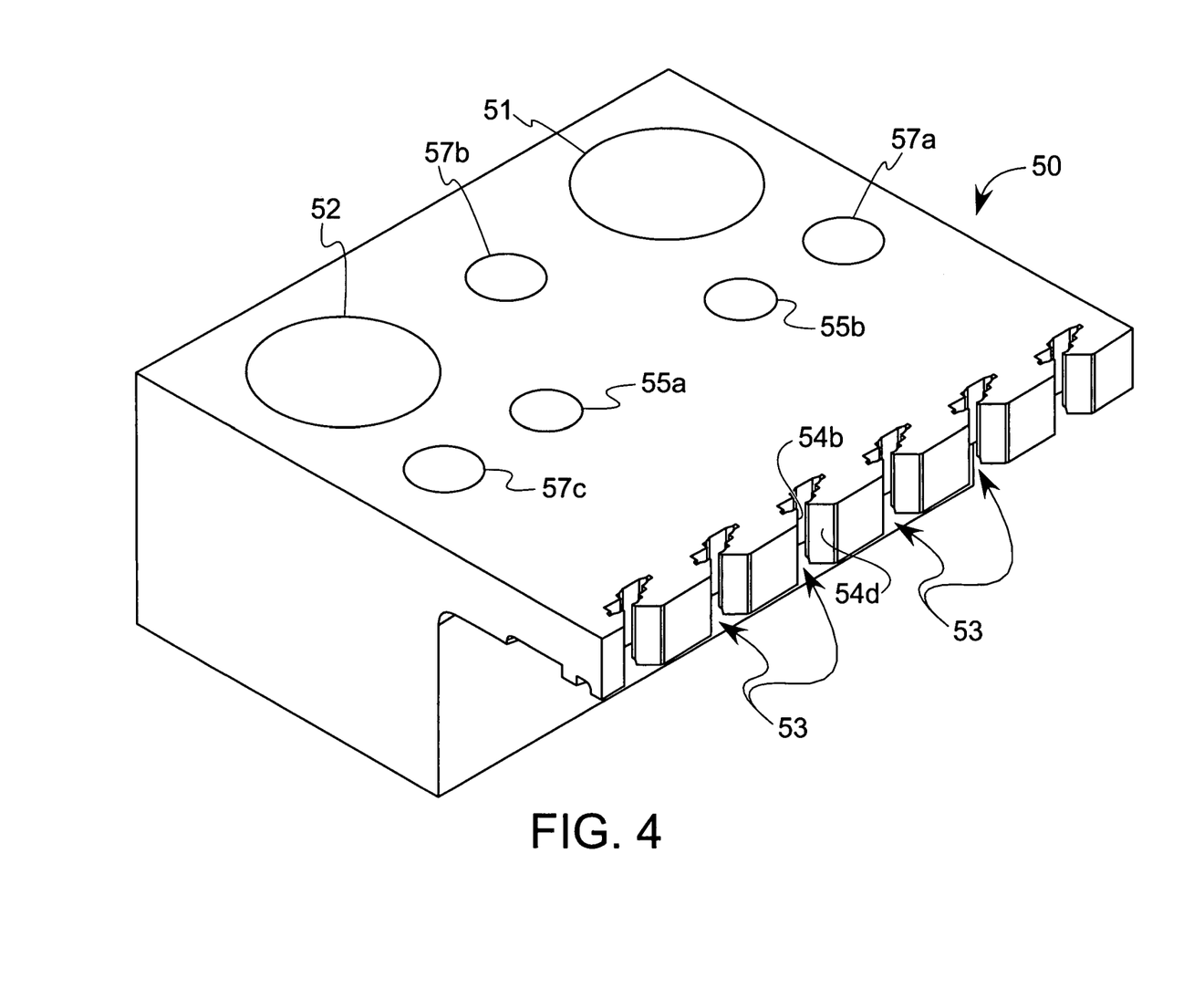
FIG. 4 is a view in perspective illustrating the preferred lower degating plate.
Figure 5:
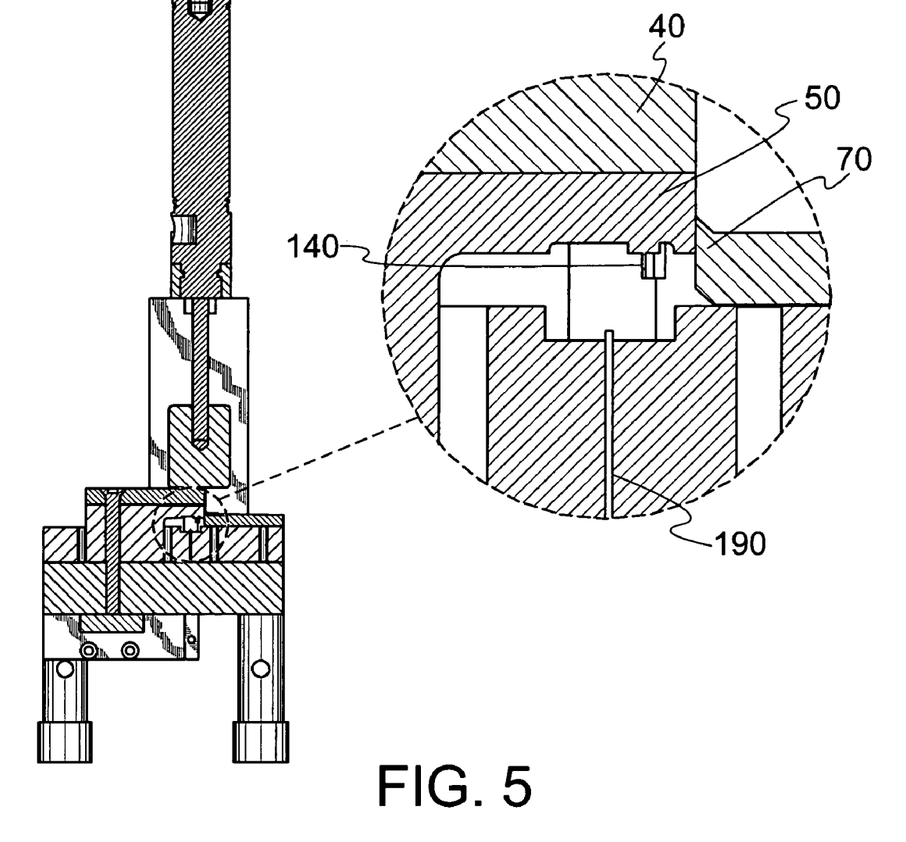
FIG. 5 is an end view in section illustrating the preferred embodiment of the present invention.

A driver guide fixture, such as the combination of the upper degating plate 40 and the lower degating plate 50 shown in FIGS. 3 and 4, respectively, is mounted to the base 12 through the opening 38 in the plate 30, leaving clearance gaps between the plates 40 and 50 and the plate 30. As shown in FIGS. 3, 4, 16, 17 and 18, three screws 60, 61 and 246 (screw 61 is not illustrated) extend through the aligned apertures 47a–47c and 57a–57c formed in the upper and lower degating plates 40 and 50, respectively, and fasten rigidly into the base 12. The screws thus mount the driver guide fixture, made up of the degating plates 40 and 50, rigidly to the base 12.

In order to align the degating plates 40 and 50 with one another, a dowel pin 240 extends tightly through the aligned apertures 45a and 55a. Another dowel pin (not illustrated) extends tightly through the aligned apertures 45b and 55b. Once the dowel pins are in place, the degating plates 40 and 50 are in precise alignment and can be mounted to the base 12.

Figure 16:
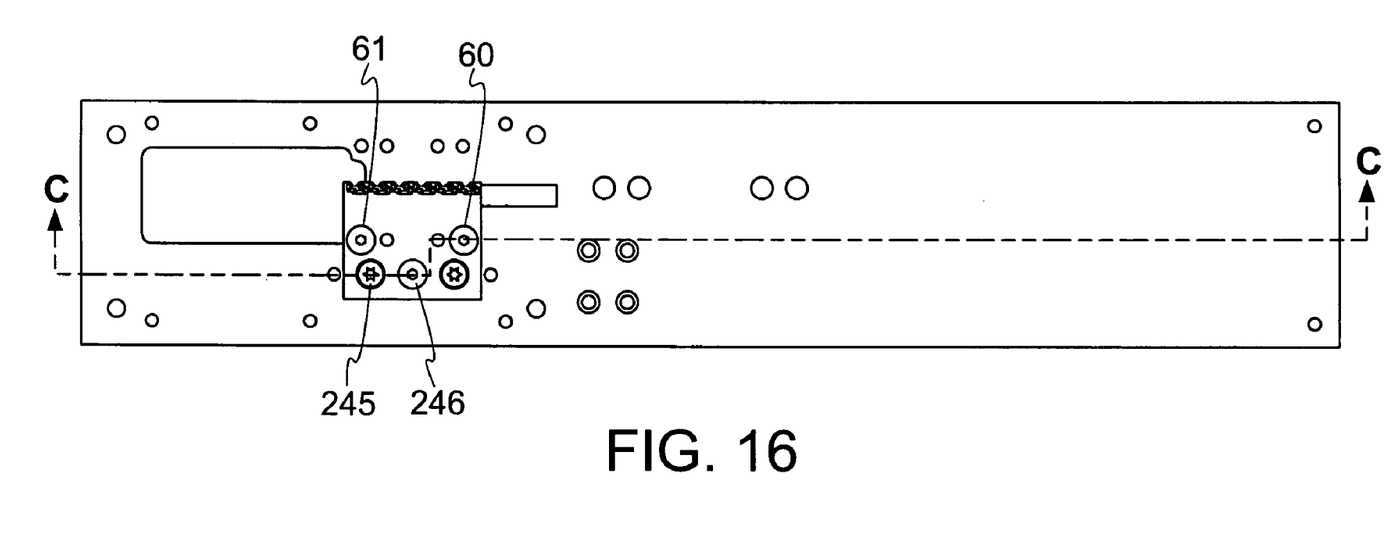
FIG. 16 is a top view illustrating the base with the degating plates mounted in a preferred position.
Figure 17:
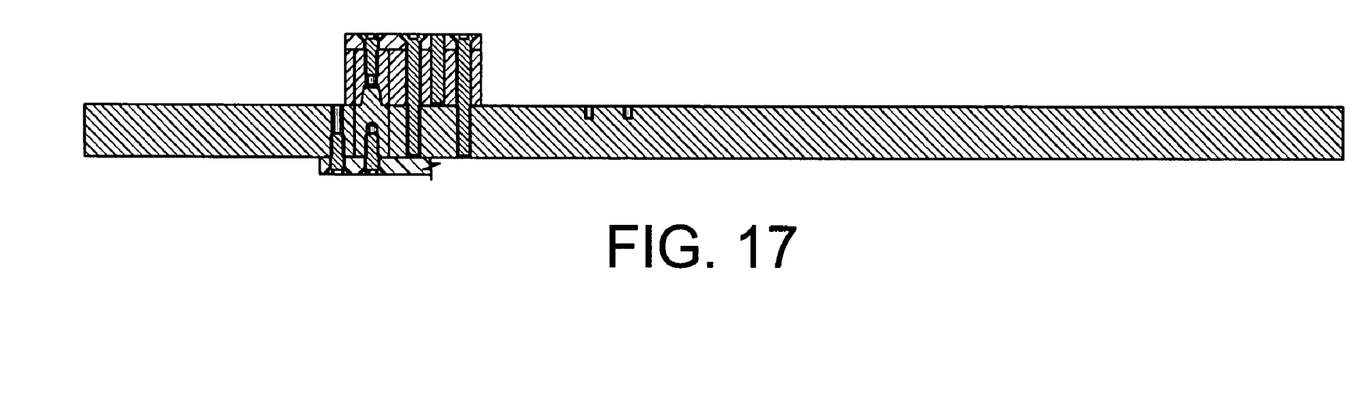
FIG. 17 is a side view in section illustrating the base of FIG. 16 through the line C—C.
Figure 18:
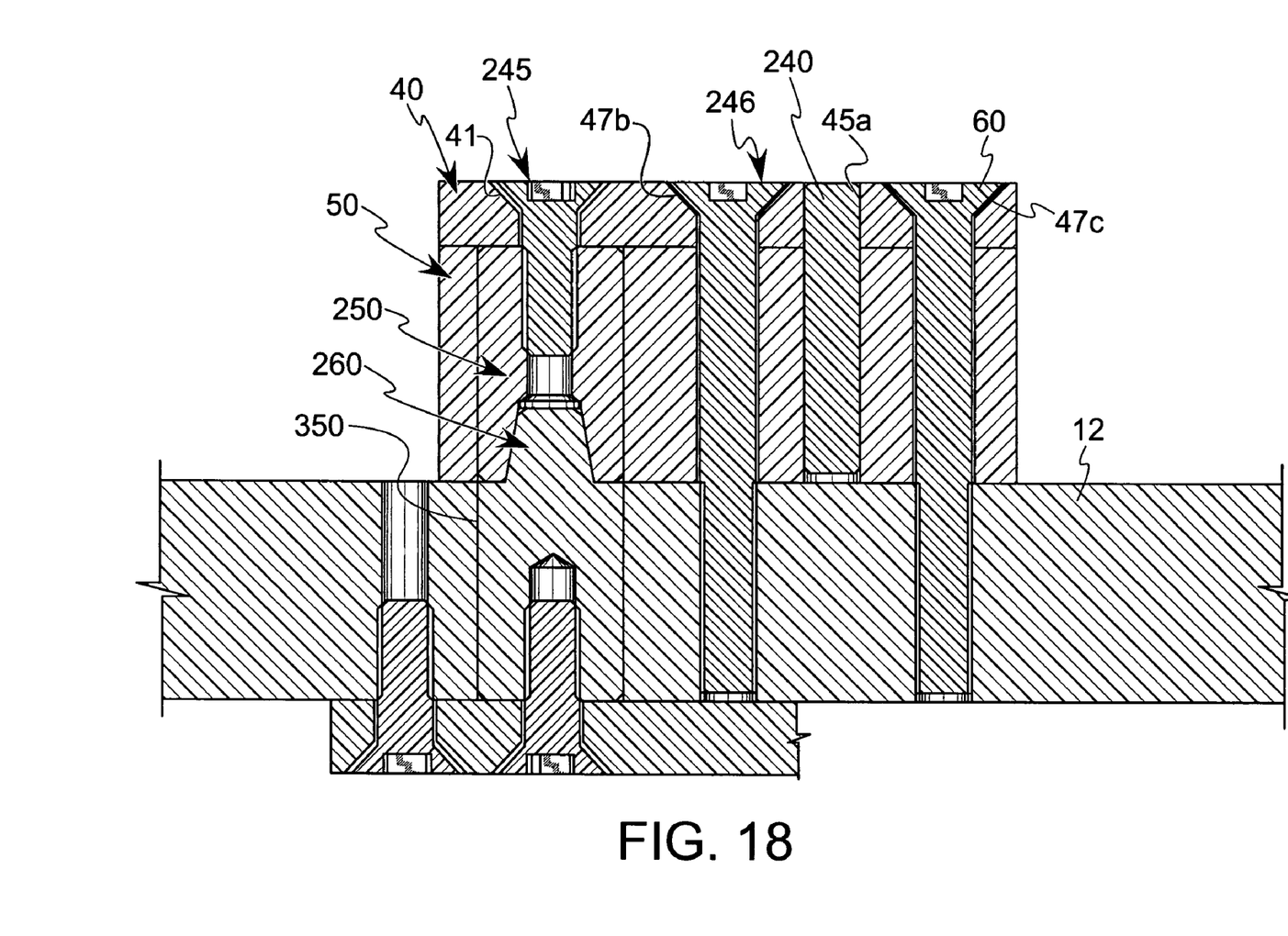
FIG. 18 is a magnified side view in section illustrating the encircled portion of FIG. 17.

One of the structures that aids in the alignment of the combined degating plates 40 and 50 with the base 12 is a taper lock locating pin 260 that fits tightly within an aperture 350 in the base 12, and its corresponding receiver 250 that fits tightly against the sidewall of the corresponding aperture 51 in the lower degating plate 50. The screw 245 extends through the aperture 41 and threads into the receiver 250 to fix the receiver 250 to the degating plates. A substantially identical taper lock locating pin and receiver (not illustrated) fit tightly in the aperture 52 and a corresponding aperture (not illustrated) in the base 12, and fasten to the degating plates at the aperture 42.

The tapered locating surfaces of the receivers align the degating plates 40 and 50 with the tapered locating pins on the base 12 so that the screws 60, 61 and 246 can be inserted through the aligned apertures in the degating plates 40 and 50 and threaded into the base 12. The dowel pins and locating pins and receivers do not permit any substantial movement of the degating plates 40 and 50 relative to one another or relative to the base 12 once the screws 60, 61 and 246 are securely mounted in the base 12.

The structures that do not permit adjustment of the degating plates 40 and 50 relative to each other or the base 12, render the degating plates 40 and 50 "non-adjustably" mounted to the base 12. The non-adjustable mounting feature permits the degating plates 40 and 50 to be removed from the base 12 and subsequently re-mounted to precisely the same position on the base 12. There is no need to align the plates 40 and 50 relative to one another or to the base 12 or any structures mounted to the base during or after fixing the parts together. By virtue of mounting the degating plates 40 and 50 on the base 12 using the screws 60, 61 and 246, the re-mounted degating plates 40 and 50 are "self-aligning", which means that they returned to the position they occupied prior to removal.

The upper degating plate 40 has a plurality of apertures 43 formed therein, extending entirely through the plate 40. The apertures 43 have tapered, converging sidewalls, which create a "funnel effect" to guide drivers inserted therein from the wider openings at the top of the plate 40 to the narrower openings at the bottom of the plate 40. The apertures 43 form a portion of the passage through the degating plates 40 and 50.

The lower degating plate 50 has apertures 53 that extend entirely through the plate 50, the upper ends of which align precisely with the lower ends of the apertures 43 in the upper degating plate 40 when the screws 60, 61 and 246 are fastened in place. The apertures 53 preferably have non-tapered sidewalls that are aligned precisely with the sidewalls of the pockets of the cartridge 300 positioned in the machine 10. Furthermore, the sidewalls of the apertures 53 very precisely match the outer surfaces of the drivers, thereby preventing any substantial lateral movement of the drivers relative to the lower degating plate 50.

Thus, upon insertion into the apertures 43 of a plurality of drivers fixed on a holder, such as a "tree with branches" holder described above, the drivers are guided toward positions aligned precisely with the apertures 53. Upon further insertion, such as by the plungers described below, the drivers are aligned precisely in the apertures 53 to be mounted in the pockets of the cartridge 300.

Figure 6:
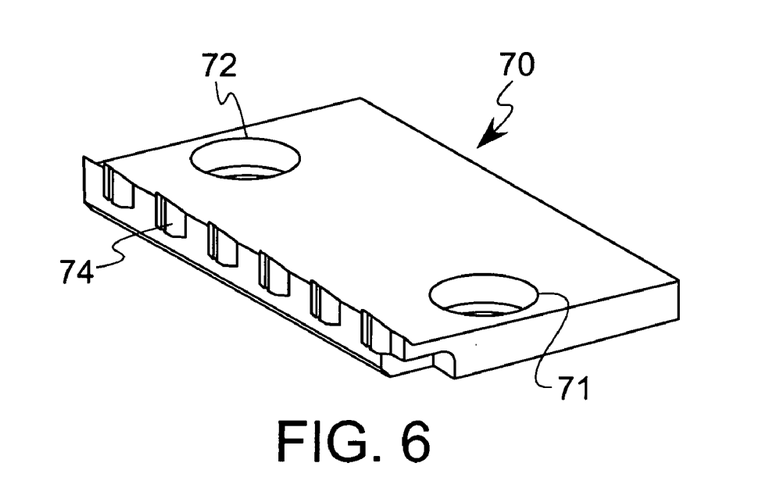
FIG. 6 is a view in perspective illustrating the preferred cutter for separating the drivers from the holders.
Figure 7:
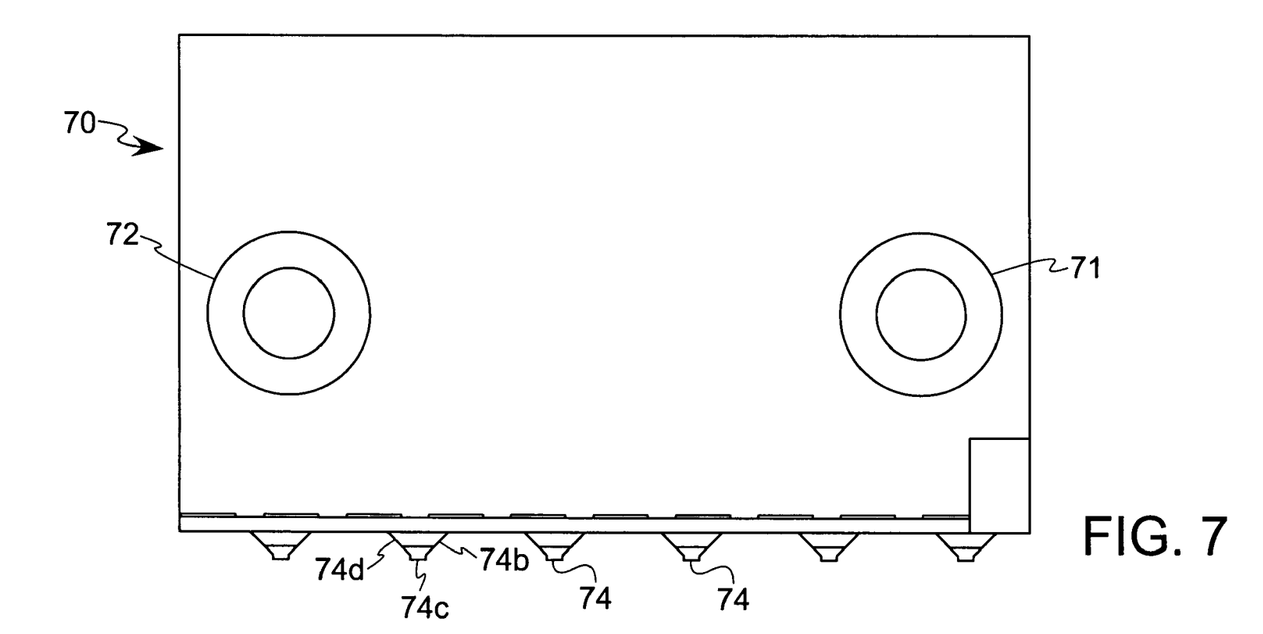
FIG. 7 is a top view illustrating the preferred cutter of FIG. 6.
Figure 8:
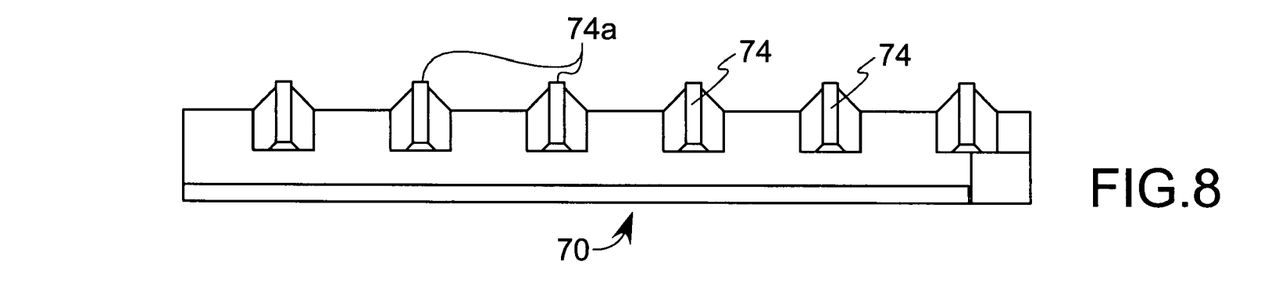
FIG. 8 is a side view illustrating the preferred cutter of FIG. 6.
Figures 9, 10:
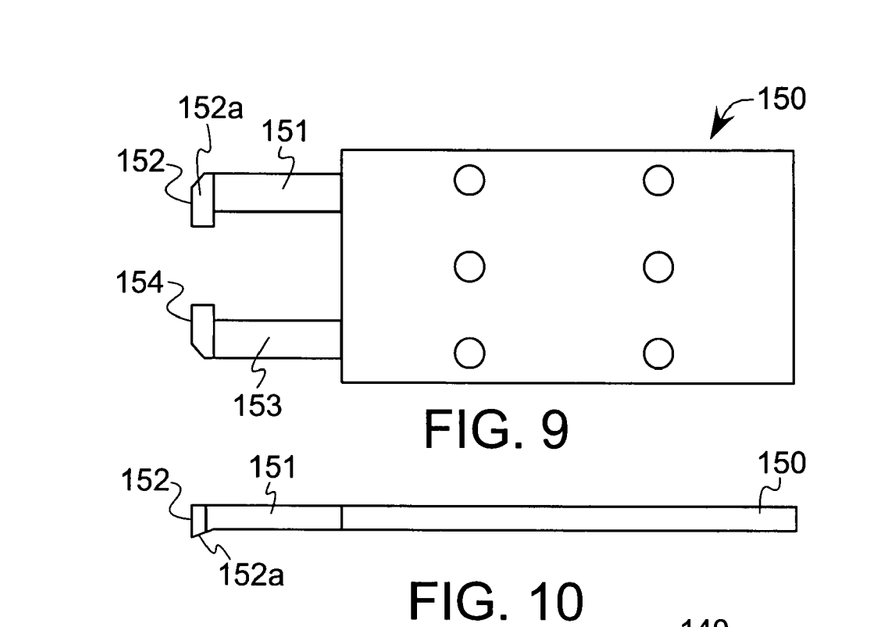
FIG. 9 is an end view illustrating the preferred cartridge-locator plate.
FIG. 10 is a side view illustrating the preferred cartridge-locator plate of FIG. 9.
Figure 11:
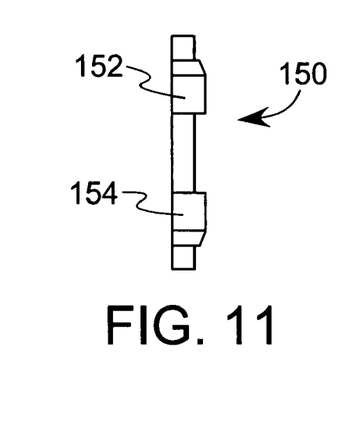
FIG. 11 is a top view illustrating the preferred cartridge-locator plate of FIG. 9.

A cutter, such as the degating knife 70 shown in FIGS. 6, 7 and 8, is mounted to the base 12 using the screws 71' and 72' (see FIG. 1) extending through the apertures 71 and 72, respectively. The screws 71' and 72' fasten rigidly to the base 12, while preventing substantial movement of the knife 70, thereby mounting the knife 70 non-adjustably to the base 12. Thus, the knife 70 can be removed and re-mounted in precisely the same location without the need for time-consuming alignment relative to other structures. The knife 70 can be made of tool steel or another material that wears well, while the degating plates 40 and 50 can be made of mild steel or another conventional, low-cost material.

In order to position the knife 70 in alignment with the degating plates 40 and 50, a plurality of aligning surfaces, such as the V-shaped surfaces of the teeth 74, are formed on the edge of the knife 70. The teeth 74 have sharp edges 74a at their upper ends for severing drivers from a holder upon downward displacement of the drivers. These sharp edges 74a are positioned precisely at the edges of the passages through which the drivers are plunged. The convex V-shaped surfaces 74b and 74d seat against the concave V-shaped surfaces 54b and 54d of the apertures 53 on the lower degating plate 50, as shown in FIG. 4. The tips 74c of the teeth 74 extend toward the apertures 53, and have the sharp edge 74a at their upper extreme thereof in the preferred embodiment at the edge of the passages.

The cooperating V-shaped surfaces of the knife 70 permit easy removal and replacement of the cutter of the machine 10, which was not previously possible. Furthermore, the knife 70 is much more easily sharpened than prior art cutting surfaces, and its alignment surfaces (e.g., 74b and 74d) are not affected by honing of the sharp edge 74a. Thus, sharpening of the knife 70 does not affect the precision with which the knife 70 is aligned at the apertures 53, because removal of material from or addition of material to the sharp edge 74a has no effect on the alignment surfaces.

Referring again to FIG. 1, a top riser 80 is adjustably mounted to the base 12, preferably using dowel pins and set screws, which, other than the set screws 82a, 82b and 83a, are not visible in FIG. 1. However, the dowel pins and set screws are structurally and functionally the same as the dowel pins and set screws that fasten the carriage-receiving plate 30 to the base 12. Thus, the top riser 80 is adjustably mounted to the base 12.

The cylinder arm 90 is rigidly and non-adjustably mounted to the top riser 80 by the screws 91 and 92 that extend through apertures formed in the cylinder arm 90 and rigidly into the top riser 80. Taper lock locating pin and receiver pairs 93 and 94 align the cylinder arm 90 with the top riser 80 in the manner described above in relation to the degating plates 40 and 50. Thus, the cylinder arm 90 can be removed from the top riser 80 and re-mounted in exactly the same position without any adjustment.

A plunger apparatus, preferably the pneumatic cylinder 100, the guides 110 and 120, the pin holder 130 and the pins 140 (see FIGS. 5, 12, 14 and 15), is mounted to the cylinder arm 90. The pneumatic cylinder 100 functions in a conventional manner to drive the pin holder 130 downwardly along a linear path, as guided by the guides 110 and 120, toward the cartridge-receiving plate 30, and then return the same to a home position. The guides 110 and 120 have bearings and smooth rods to maintain the linear path of the pin holder 130. The bearings provide substantially no resistance to the longitudinal movement of the rods, but substantial resistance to lateral movement of the rods.

Figure 12:
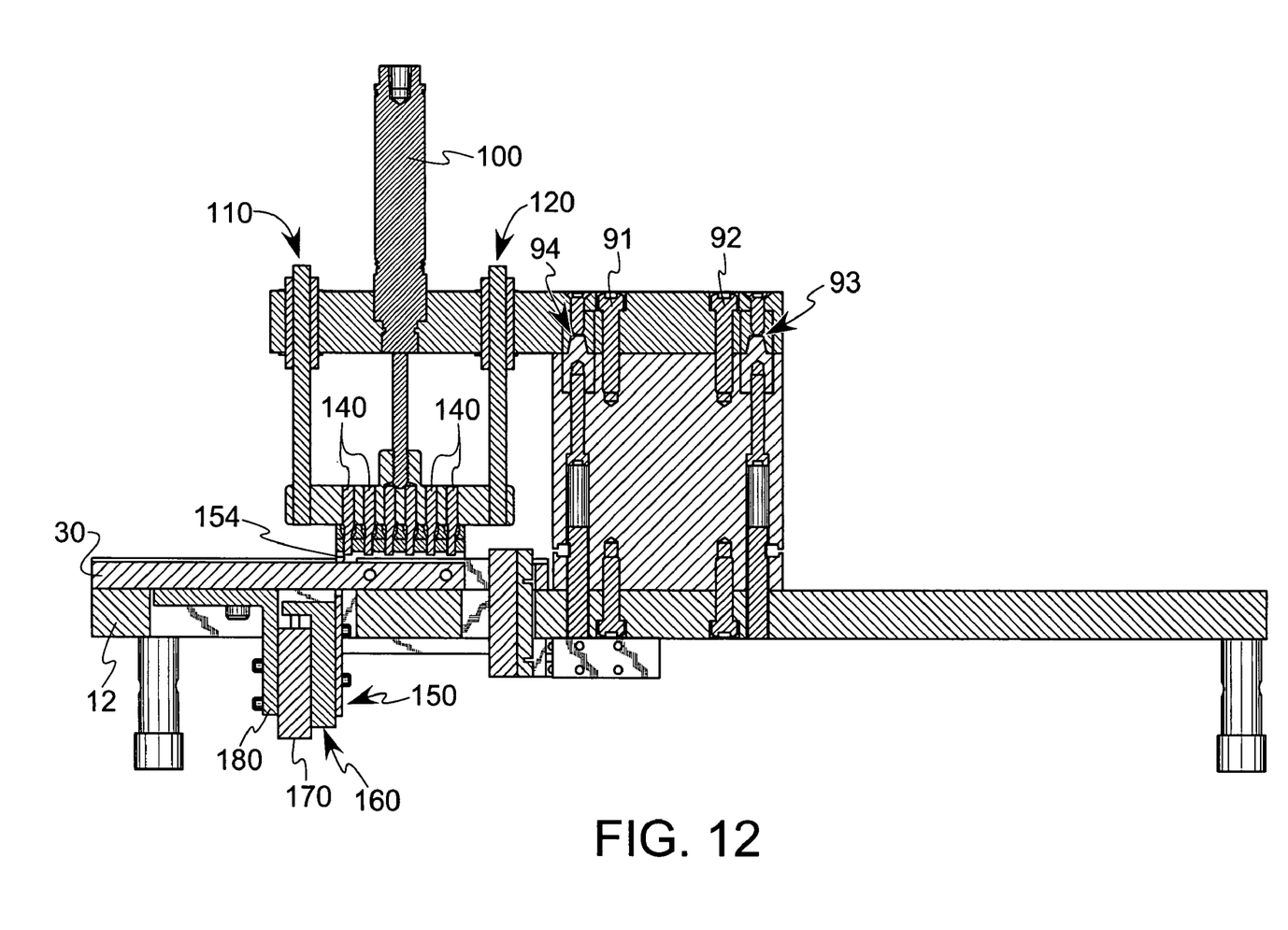
FIG. 12 is a side view illustrating the preferred embodiment of the present invention.
Figure 14:
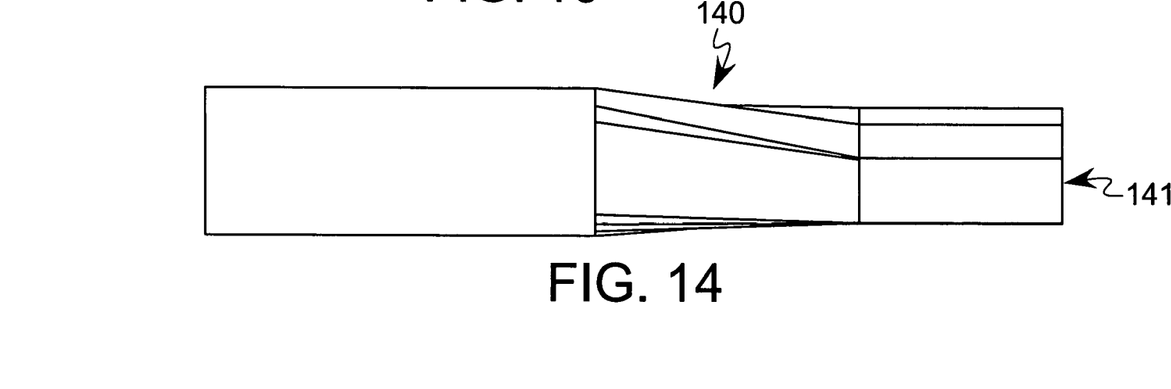
FIG. 14 is a side view illustrating a preferred pin.
Figure 15:
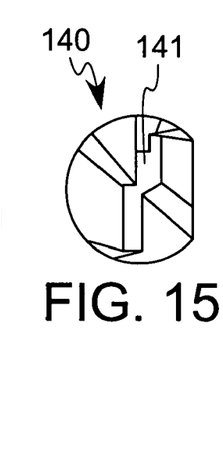
FIG. 15 is a bottom view illustrating a preferred pin.

A plurality of pins 140, such as the pin 140 shown in FIGS. 14 and 15, is mounted to the pin holder 130 aligned in a pattern that permits the pins 140 to be plunged directly into the passages in the degating plates 40 and 50, as shown in FIG. 12. The preferred pins 140 have a tip surface 141 that closely matches the surface of the drivers with which the pin 140 will make contact. Thus, there is a substantially complete contact by the pins 140 with the entire upper surface of the drivers. This improves the performance of the machine 10.

The locator plate 150, illustrated in FIGS. 9, 10, 11 and 12, is a substantially planar structure having a pair of legs 151 and 153 that extend from the main body and terminate in tips 152 and 154, respectively. Between the legs 151 and 153 is a gap large enough for the cartridge to be extended through. The tips 152 and 154 have angled faces, such as the face 152a, shown in FIGS. 10 and 13. The tip 154 has a similarly angled face that is not visible in the drawings.

Referring to FIG. 12, the locator plate 150 is mounted to a rigid, L-shaped member 160 that is in contact with the moveable arm of the pneumatic ram 170. The ram 170 is rigidly mounted to a rigid, L-shaped member 180, which is rigidly mounted to the underside, in the orientation shown in FIG. 12, of the cartridge-receiving plate 30. In this configuration, the legs 151 and 153 extend upwardly from the main body of the locator plate 150 through the grooves 251 and 253, respectively, formed in the cartridge-receiving plate 30. This is best viewed in FIGS. 2 and 13.

The tips 152 and 154 extend above the channel 35 in the cartridge-receiving plate 30 as shown in the lowered position in FIGS. 1, 12 and 13. When the locator plate 150 is in its home position, the tips 152 and 154 are significantly above the channel floor 35c from the position shown in FIG. 13, in order for a cartridge to be inserted through the gap between the legs 151 and 153. Once the cartridge 300 is in place, the ram 170 is actuated to displace the locator plate 150 downwardly to the position shown in FIG. 13. This downward force seats the angled face 152a and the angled face on the tip 154 against the end of the cartridge 300, and as the locator plate 150 is displaced downwardly, the "wedge effect" of the angled face forces the cartridge 300 away from the legs 151 and 153, which forces an opposing surface of the cartridge 300 against the stops 36 and 37 as shown in FIG. 13. This locates the cartridge 300 in an exact position, and holds the cartridge 300 in that position during the driver insertion process.

Referring again to FIGS. 2 and 5, a cartridge-locating blade 190 is mounted in the slot 192 formed in the cartridge-receiving plate 30. The cartridge 300 has a longitudinal slot in its underside, into which the blade 190 extends during insertion of the cartridge 300 into the machine 10. The blade 190 thus laterally locates the cartridge 300 during insertion of the cartridge 300 in the channel 35, and laterally restrains the cartridge 300 during insertion of the drivers. It is preferred that the blade 190 only extend a portion of the height of the slot, rather than the entire height, as is conventional, in order to avoid distortion of the cartridge walls. In one contemplated dimension, the blade 190 extends approximately 0.020 inches into a slot that is at five times that height.

In the preferred embodiment, the pneumatic rams on the machine 10 are connected to a central computer 200, illustrated in FIG. 1. The central computer 200 can be any device capable of logical operations, and is preferably either a single-purpose logic circuit or a multipurpose, programmable microcomputer. Of course, a mechanical computer or any other such device will suffice. The computer 200 is connected to a switch 210, which is depressed by a user of the machine when insertion of the drivers is desired. Sensors are preferably connected to the computer 200 to signal the computer 200 when the rams 100 and 170 are at their extreme positions. These sensors can be internal to the rams, or they can be conventional sensors that permit detection of the position of the moving parts of the rams 100 and 170 and signaling of the computer 200. Examples of such sensors, which the person of ordinary skill will recognize are not the only such devices to be useful, include proximity sensors, optical sensors, mechanical switches, etc.

The machine 10 operates as follows. A cartridge 300 is inserted into the channel 35 and through the gap between the legs 151 and 153 until the cartridge 300 seats against the stops 36 and 37 with the locator blade 190 in the longitudinal slot of the cartridge as shown in FIG. 13. Before or after the cartridge 300 is inserted in the machine 10, a staple driver holder, with drivers mounted to its tips, is manually placed in the machine 10 with the drivers in the apertures 43 of the upper degating plate 40.

Once the drivers are in place in the degating plate 40, the machine is actuated, such as by depressing the mechanical switch 210, which signals the computer 200 to begin the driver insertion process. The computer 200 first actuates the pneumatic ram 170 to draw the locator plate 150 downward, thereby locating and holding the cartridge 300 against the stops 36 and 37 as shown in FIG. 13. Once the locator plate 150 has been displaced downward to its cartridge-locating position, as detected by a sensor as described above, the computer 200 actuates the ram 100 to displace the pin holder 130 and the pins 140 mounted thereon downwardly toward the cartridge 300. While plunging downwardly, the pins 140, which are aligned with the passages in the degating plates 40 and 50, and the pockets in the cartridge, drive the drivers downwardly until the holders contact and pass further by the sharp edges 74a of the knife 70. This motion severs the drivers from the holder and permits the pins 140 to plunge the drivers down further in the passages and into the pockets of the cartridge 300.

Upon reaching the lower extreme of its cycle (shown in FIGS. 1, 5 and 12) as sensed by a sensor as described above, the computer 200 actuates the ram 100 to return the pin holder 130 and attached pins 140 to their home position. Once the ram 100 reaches its home position, or possibly before, the computer 200 actuates the ram 170 to displace the locator plate 150 upwardly, which permits the cartridge 300 to be removed from the channel 35. In a preferred embodiment, a conventional ejector (not shown) is used to eject the cartridge 300 from the channel 35.

When the machine 10 requires maintenance, such as sharpening of the knife 70, replace the degating plates 40 or 50, or one of the pins 140, such maintenance can be accomplished without the need to realign all of the parts of the machine 10. For example, removal of the knife 70 can occur simply by removing the screws 71' and 72'. The knife 70 is then taken to a machine and the sharp edges 74a are ground down slightly until they are sufficiently sharp. If more material needs to be added to the knife 70, such as due to severe wear, this can also be accomplished at this time. Upon completion, the knife 70 is re-mounted in place simply by inserting and fixing the screws 71' and 72'. No adjustment is necessary, because the V-shaped surfaces of the knife 70 register with the V-shaped surfaces of the lower degating plate 50, thereby precisely aligning the knife 70, and when the screws 71' and 72' are tightened in place the knife 70 is in the exact position from which it was taken.

Likewise, if the upper and lower degating plates 40 and 50 need maintenance, they can be removed by removing the screws 60, 61 and 246 and removing the plates 40 and 50 from the base 12. Re-mounting of the plates merely requires replacing the screws 60, 61 and 246. The plates 40 and 50 have only one position relative to the base 12 when the screws are fastened to the base 12, and that position is the same every time the plates are mounted as shown.

The cylinder arm 90 can also be removed from the top riser 80 by removing the screws 91 and 92. After maintenance, such as to replace a pin 140, the cylinder arm 90 can be re-mounted merely by aligning the taper lock surfaces and inserting the screws 91 and 92 in the cylinder arm 90 and fixing them to the top riser 80. No adjustment is needed to align the parts that were removed and re-mounted.

When the machine 10 is first assembled, or when alignment of parts becomes necessary due to, for example, adapting the machine 10 to a different type of cartridge, all of the parts that have to be precisely aligned to other parts are aligned with greater ease and precision than in prior art machines.

For example, the cartridge-receiving plate 30 is aligned relative to the passages in the degating plates 40 and 50, and the knife 70 by loosening and/or tightening the set screws that seat against the dowel pins 31–34 that extend from rigid attachment to the base through the apertures 31'–34' at the corners of the cartridge-receiving plate 30. This alignment between the cartridge-receiving plate 30 and the passages in the degating plates 40 and 50 must be precise, because it determines the alignment between the passages in the degating plates 40 and 50 and the pockets in the cartridges that will have drivers inserted into them.

It is important to note that the cartridge-receiving plate 30 can be displaced relative to the base 12 in order to precisely align the cartridge-receiving plate 30 with the degating plates 40 and 50 and the knife 70. According to the invention, the degating plates 40 and 50 and the knife 70 are not adjustable relative to the base 12. Instead, they are self-aligning back to their original position. This produces one significant advantage of the invention: the structures that rarely need to be removed from the base 12, such as the cartridge-receiving plate 30, are adjustable relative to the base, but the objects that often need to be removed from the base 12, such as the degating plates 40 and 50, are not adjustable, but are self-aligning. This cooperation of features results in a machine 10 in which re-mounting the often-removed objects does not require realignment of any structures on the machine 10. Instead, only the removal and re-mounting of rarely removed objects necessitates realignment. This saves a substantial amount of time in maintaining the equipment.

After the cartridge-receiving plate 30 is aligned relative to the degating plates, the top riser 80 can be displaced slightly relative to the base 12 in order to align the pins 140 with the passages on the degating plates 40 and 50. In the preferred embodiment, this is accomplished by set screws and dowel pins similar to those on the cartridge-receiving plate 30, thus permitting the user to precisely align the structures mounted to the top riser 80 relative to other objects. The cylinder arm 90 is mounted to the top riser 80 with no adjustability, and therefore one can remove and re-mount the cylinder arm 90 and its attached parts very quickly and to precisely the same position from which it was removed. Thus, if the cylinder arm 90 needs to be removed to replace a pin 140, which is a frequent maintenance task, it can be accomplished with no need for alignment or adjustment of the cylinder arm 90 relative to the top riser 80.

While certain preferred embodiments of the present invention have been disclosed in detail, it is to be understood that various modifications may be adopted without departing from the spirit of the invention or scope of the following claims.

The invention claimed is:

1. An apparatus for inserting at least one driver into at least one pocket formed in a surgical staple cartridge, the apparatus comprising:
   (a) a base;
   (b) a cartridge-receiving plate rigidly and adjustably mounted to said base, the cartridge-receiving plate having a channel configured to receive a cartridge;
   (c) a driver guide fixture rigidly mounted to the base adjacent the channel of the cartridge-receiving plate, the guide fixture having a passage formed therein to receive and guide said at least one driver into the cartridge during use, said guide fixture passage having
(i) a first portion with converging, tapered walls; and
(ii) a second portion with walls having dimensions for fitting closely around at least part of the driver;
(d) a cutter rigidly mounted to said base adjacent the channel of the cartridge-receiving plate, the cutter having at least one sharp edge for severing said at least one driver from a driver holder, said at least one sharp edge disposed at an edge of the passage of the driver guide fixture, wherein the cutter is removable from the base separate from the driver guide fixture; and
(e) a plunger apparatus having an element aligned with the fixture passage and configured to force the driver toward the fixture passage, thereby causing the driver holder to engage the sharp edge of the cutter and separate the driver from the driver holder, the driver continuing on into said at least one pocket of the cartridge.

2. The apparatus in accordance with claim 1, wherein the cutter is non-adjustably mounted to the base.

3. The apparatus in accordance with claim 2, wherein the guide fixture is non-adjustably mounted to the base.

4. The apparatus in accordance with claim 3, further comprising at least one stop mounted near the channel of the cartridge-receiving plate and a cartridge locator plate extending into the channel for seating against the cartridge and forcing the cartridge against said at least one stop.

5. The apparatus in accordance with claim 4, wherein a tip of the plunger apparatus element substantially matches a surface of said at least one driver against which the element seats during engagement with said at least one driver.

6. The apparatus in accordance with claim 5, wherein each of a plurality of dowels extend from rigid attachment to the base loosely through one of a plurality of corresponding openings in the cartridge-receiving plate, and a plurality of set screws extend through the cartridge-receiving plate into the openings and seat against the dowels.

7. The apparatus in accordance with claim 6, wherein said at least one driver comprises a plurality of drivers, and said at least one pocket comprises a plurality of pockets, and wherein each of said drivers is inserted into one corresponding pocket.

8. The apparatus in accordance with claim 5, further comprising a top riser rigidly and adjustably mounted to the base, and an arm rigidly and non-adjustably mounted to the top riser, wherein the plunger apparatus rigidly and non-adjustably mounts to said arm.

9. The apparatus in accordance with claim 8, wherein the guide fixture comprises an upper degating plate in which the first portion of the passage is formed, and a lower degating plate in which the second portion of the passage is formed.

10. The apparatus in accordance with claim 9, further comprising a cartridge-locating blade extending into the channel for insertion into a slot in the cartridge.

11. The apparatus in accordance with claim 2, further comprising a plurality of surfaces on the cutter that register with cooperating surfaces on the guide fixture.

12. A method of inserting at least one driver into at least one pocket formed in a surgical staple cartridge, the method comprising:
(a) mounting a cartridge-receiving plate to a base, the cartridge-receiving plate having a channel configured to receive a cartridge;
(b) mounting a driver guide fixture rigidly to the base adjacent the channel of the cartridge-receiving plate, the guide fixture having a passage formed therein to receive and guide said at least one driver into the cartridge during use, said guide fixture passage having
(i) a first portion with converging, tapered walls; and
(ii) a second portion with walls having dimensions for fitting closely around at least part of the driver;
(c) mounting a cutter rigidly to said base adjacent the channel of the cartridge-receiving plate, the cutter having at least one sharp edge disposed at an edge of the guide fixture passage;
(d) adjusting a position of the cartridge-receiving plate relative to the base to align the channel with the guide fixture passage;
(e) adjusting a position of an element of a plunger apparatus relative to the base to align the element with the guide fixture passage;
(f) disposing the cartridge in the channel;
(g) disposing said at least one driver in the guide fixture passage;
(h) driving the plunger into engagement with said at least one driver, forcing the driver through the guide fixture passage, forcing a driver holder against the sharp edge of the cutter, separating the driver from the driver holder and forcing the driver into said at least one pocket of the cartridge; and
(i) withdrawing the plunger from the guide fixture passage.

13. The method in accordance with claim 12, wherein said at least one driver comprises a plurality of drivers and said at least one pocket comprises a plurality of pockets, and further comprising repeating steps (g), (h) and (i) for all drivers.

14. The method in accordance with claim 12, further comprising removing the cutter from the base separate from the guide fixture.

15. The method in accordance with claim 14, further comprising:
(a) sharpening said at least one sharp edge of the cutter; and
(b) re-mounting the cutter to the base without adjustment relative to the guide fixture.

16. The method in accordance with claim 12, further comprising removing the guide fixture from the base separate from the cutter.

17. The method in accordance with claim 16, further comprising re-mounting the guide fixture to the base without adjustment relative to the cutter.

18. The method in accordance with claim 12, further comprising extending a cartridge locator plate into the channel for seating against the cartridge and forcing the cartridge against a stop mounted near the channel.

19. The method in accordance with claim 18, further comprising adjustably mounting a top riser rigidly to the base, non-adjustably mounting an arm rigidly to the top riser, and mounting the plunger apparatus rigidly and non-adjustably to the arm.

20. The method in accordance with claim 19, further comprising extending a cartridge-locating blade into a slot in the cartridge.

21. The method in accordance with claim 18, further comprising detecting a position of the cartridge locator plate.

22. The method in accordance with claim 12, further comprising detecting a position of the plunger.

* * * * *